(12) United States Patent
Nitta et al.

(10) Patent No.: US 8,728,050 B2
(45) Date of Patent: May 20, 2014

(54) ABSORBENT ARTICLE PROVIDED WITH A BARRIER SHEET

(75) Inventors: Reiko Nitta, Kagawa (JP); Kaiyo Nakajima, Kagawa (JP); Hironao Minato, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 1003 days.

(21) Appl. No.: 12/808,551

(22) PCT Filed: Aug. 18, 2008

(86) PCT No.: PCT/JP2008/064694
§ 371 (c)(1),
(2), (4) Date: Feb. 11, 2011

(87) PCT Pub. No.: WO2009/081617
PCT Pub. Date: Jul. 2, 2009

(65) Prior Publication Data
US 2011/0125121 A1 May 26, 2011

(30) Foreign Application Priority Data

Dec. 20, 2007 (JP) ................................. 2007-329235

(51) Int. Cl.
*A61F 13/15* (2006.01)
*A61F 13/20* (2006.01)

(52) U.S. Cl.
USPC ................. 604/385.201; 604/385.01; 604/396

(58) Field of Classification Search
USPC ......... 604/385.01, 385.201, 385.09, 385.101, 604/385.11, 395, 398
See application file for complete search history.

(56) References Cited

U.S. PATENT DOCUMENTS

| 7,670,325 | B2 | 3/2010 | Sugiyama et al. | |
| 8,303,559 | B2 * | 11/2012 | Minato et al. | 604/385.19 |
| 2004/0039363 | A1 | 2/2004 | Sugiyama et al. | |
| 2006/0135931 | A1 * | 6/2006 | Suzuki et al. | 604/385.19 |
| 2009/0005752 | A1 * | 1/2009 | Suzuki et al. | 604/385.101 |

FOREIGN PATENT DOCUMENTS

| JP | 53044536 U | 4/1978 |
| JP | 2000-296148 A | 10/2000 |
| JP | 2002011044 A | 1/2002 |
| JP | 2002204811 A | 7/2002 |
| JP | 2007-105298 A | 4/2007 |
| JP | 2007130442 A | 5/2007 |

OTHER PUBLICATIONS

ISR for PCT/JP2008/064694 dated Nov. 25, 2008.

* cited by examiner

*Primary Examiner* — Michele M Kidwell
(74) *Attorney, Agent, or Firm* — Lowe Hauptman & Ham LLP (57) ABSTRACT

The present invention aims to provide an absorbent article with a barrier sheet preventing body waste from coming in contact with a wearer's skin and thereby to alleviate skin trouble such as eczema the wearer might suffer from. The article includes an absorbent chassis, a barrier sheet and a leak-barrier cuffs. An absorbent panel is disposed on the inner surface of the chassis, the barrier sheet is disposed above the absorbent panel and the leak-barrier cuffs are disposed along a lateral side of the barrier sheet. The barrier sheet has lateral zones a middle zone connecting the lateral zones, and front and rear through-holes defined by the lateral zones and the middle zone. Barrier sheet elastic members are provided along the lateral zones. Folds are formed so as to cross the middle zone in a transverse direction.

5 Claims, 8 Drawing Sheets

ABSORBENT ARTICLE PROVIDED WITH A BARRIER SHEET

RELATED APPLICATIONS

The present application is national phase of International Application Number PCT/JP2008/064694, filed Aug. 18, 2008, and claims priority from, Japanese Application Number 2007-329235, filed Dec. 20, 2007, the disclosures of which are hereby incorporated by reference herein in their entirety.

TECHNICAL FIELD

The present invention relates to absorbent articles and more particularly to absorbent articles such as disposable diapers, toilet-training pants or incontinent briefs.

RELATED ART

Disposable diapers provided with skin-contact sheets serving to protect the wearers' skin from contact with body waste are known, for example, from the disclosure of JP2007-105298A (PATENT DOCUMENT 1). According to the disclosure of PATENT DOCUMENT 1, the diaper comprises a topsheet, a backsheet, an absorbent structure sandwiched between these topsheet and backsheet and a skin-contact sheet disposed on the side of the topsheet facing a wearer's skin wherein the skin-contact sheet is provided with at least one through-hole adapted to guide body waste to the side of the topsheet and elastic members attached under tension to the skin-contact sheet so as to surround the through-hole. Such skin-contact sheets adopted by these two examples of prior art are adapted to raise themselves from the topsheets and to come in contact with the wearers' crotch skin under the effect of the elastic members so as to protect the wearer's skin from contact with body waste.
PATENT DOCUMENT 1: JP2007-105298A

DISCLOSURE OF THE INVENTION

Problem to be Solved by the Invention

In the diaper disclosed in PATENT DOCUMENT 1, a through-hole giving passage to urine and a through-hole giving passage to feces are provided. However, the diaper may displace on a wearer's body depending on a posture of the wearer and consequently sometimes urination occurs directly on the skin contact sheet. Urine staying on the skin contact sheet may cause stuffiness and any skin trouble such as eczema.

In view of the problem as has been described just above, it is a principal object of the invention to prevent urine on the barrier sheet from coming in contact with a wearer's skin and thereby to alleviate skin trouble such as eczema the wearer might suffer from.

Measure to Solve the Problem

The invention relates to an improvement in the absorbent article comprising a chassis having a front-to-rear direction and a transverse direction, sides facing a wearer's skin and wearer's clothes, respectively, a front waist region, a rear waist region and a crotch region extending between the front and rear waist regions, and a liquid-absorbent structure disposed on the crotch region, and a barrier sheet provided in the crotch region on the side of the chassis facing a wearer's skin and being able to be spaced from the chassis.

The absorbent article according to the invention is characterized in that the barrier sheet has a pair of lateral zones extending in the front-to-rear direction and opposed to each other in the transverse direction, a middle zone connecting the lateral zones to each other, front and rear ends extending in the transverse direction and opposed to each other in the front-to-rear direction and barrier sheet's elastic members extending in the front-to-rear direction and attached under tension to the barrier sheet and opposed to each other in the transverse direction wherein the front and rear ends are permanently bonded to the side of the chassis facing a wearer's skin and the liquid-absorbent structure is adapted to be bowed in a direction from the crotch region toward the front and rear waist regions and thereby to form a pocket between the barrier sheet and the liquid-absorbent structure, and to form through-holes defined by the pair of lateral zones and the middle zone so that body waste can pass the through-holes into the pocket, and the pair of lateral zones lying outside the middle zones as viewed in the transverse direction are formed with folds along which the barrier sheet is convex toward the chassis.

According to one preferred embodiment, the folds are formed by thermal processing, e.g., fusing the portions of the lateral zones.

According to another preferred embodiment, the folds are formed by folding portions of the lateral zones so as to be convex toward the side of the chassis and bonding the opposite surfaces of the portions folded in this manner.

According to still another preferred embodiment, the barrier sheet includes the slits formed by partially cutting off the folds.

According to yet another preferred embodiment, the liquid-absorbent structure is bonded to the lateral zones of the barrier sheet via the joint zones and these joint zones lie inside the side edges as viewed in the transverse direction wherein the side edges are extending in the front-to-rear direction of the liquid-absorbent structure and opposed to each other in the transverse direction so that the exposed portions not covered with the barrier sheet appear along the side edges of the liquid-absorbent structure when the barrier sheet is spaced upward from the chassis.

According to further another preferred embodiment, the through-hole comprises the front through-hole defined on the front side with respect to the middle zone as viewed in the front-to-rear direction and the rear through-hole defined on the rear side with respect to the middle zone as viewed in the front-to-rear direction wherein the barrier sheet's elastic members are attached to the barrier sheet along the front and rear through-holes and, respectively include the convex segments extending toward the longitudinal center line bisecting the dimension of the barrier sheet in the middle zone and wherein the folds lie outside the barrier sheet's elastic members as viewed in the transverse direction.

Effect of the Invention

According to the invention, the lateral zones of the barrier sheet defined just outside the middle zone as viewed in transverse direction are formed with the folds extending in the transverse direction so that the barrier sheet can be folded convexly toward the chassis along these folds. Such unique arrangement ensures that, even when urination occurs onto the barrier sheet, urine moving to the middle zone defined by these folds is reliably guided thereby toward the chassis. In this way, urine is prevented from staying on the barrier sheet and causing any skin trouble.

According to the embodiment of the invention wherein the folds are formed fusing the portions of the lateral zones of the barrier sheet so as to form the grooves, the folds are guided so as to be easily folded along the grooves.

According to the embodiment of the invention wherein the barrier sheet include the slits formed by partially cutting off the folds, the zones in which the slits are formed have a sufficiently low rigidity to facilitate the barrier sheet to be folded along the folds. The slits allow urine staying on the barrier sheet to be quickly through the slits to the liquid-absorbent structure.

According to the embodiment of the invention wherein the barrier sheet is bonded to the liquid-absorbent structure via the joint zones, and the joint zones lie inside the side edges of the liquid-absorbent structure and therefore, when the barrier sheet is spaced upward from the liquid-absorbent structure, the portion of the liquid-absorbent structure not covered with both the barrier sheet and leak-barrier cuffs is defined between the side edges and the joint zones. Thus, urine otherwise staying on the barrier sheet can be guided along the folds to the liquid-absorbent structure and absorbed therein.

According to the embodiment of the invention wherein the through-hole formed to the barrier sheet comprises the front through hole defined on the front side with respect to the middle zone and the rear through-hole defined on the rear side with respect to the middle zone wherein the barrier sheet's elastic members are attached to the barrier sheet along the front and rear through-holes and therein the folds lie outside the barrier sheet's elastic members, contractile force of the barrier sheet's elastic members directed from the lateral zones toward the longitudinal center line is exerted on the middle zone, further facilitating the lateral zones along the folds. Furthermore, since the barrier sheet's elastic members has a convex segment in the middle zone of the barrier sheet, the barrier sheet's elastic members cause the middle zone into better contact with the wearer's skin and the barrier sheet is folded along the folds so as to stop from the middle zone toward the liquid-absorbent structure. Consequently, urine staying on the barrier sheet can be quickly guided from the middle zone to the liquid-absorbent structure via the lateral zones.

IDENTIFICATION OF REFERENCE NUMERALS USED IN THE DRAWINGS 1 diaper
2 chassis
3 barrier sheet
4 leak-barrier cuffs
5 side facing wearer's skin
6 side facing away from wearer's skin
7 front waist region
8 rear waist region
9 crotch region
10 liquid-absorbent structure
27 front end
28 rear end
29 pocket
30 lateral zone
31 lateral zone
32 middle zone
33 front through-hole
34 rear through-hole
39 barrier sheet's elastic members
40 curved segments
43 joint zones
44 side edge
45 side edge
49 side edges
50 cuffs' elastic members
54 slits

DESCRIPTION OF THE BEST MODE FOR WORKING OF THE INVENTION

The present invention will be exemplarily described hereinafter on the basis of a disposable diaper taken as typical embodiments of an absorbent article according to the present invention.

First Embodiment According to the Invention

Figure 1:
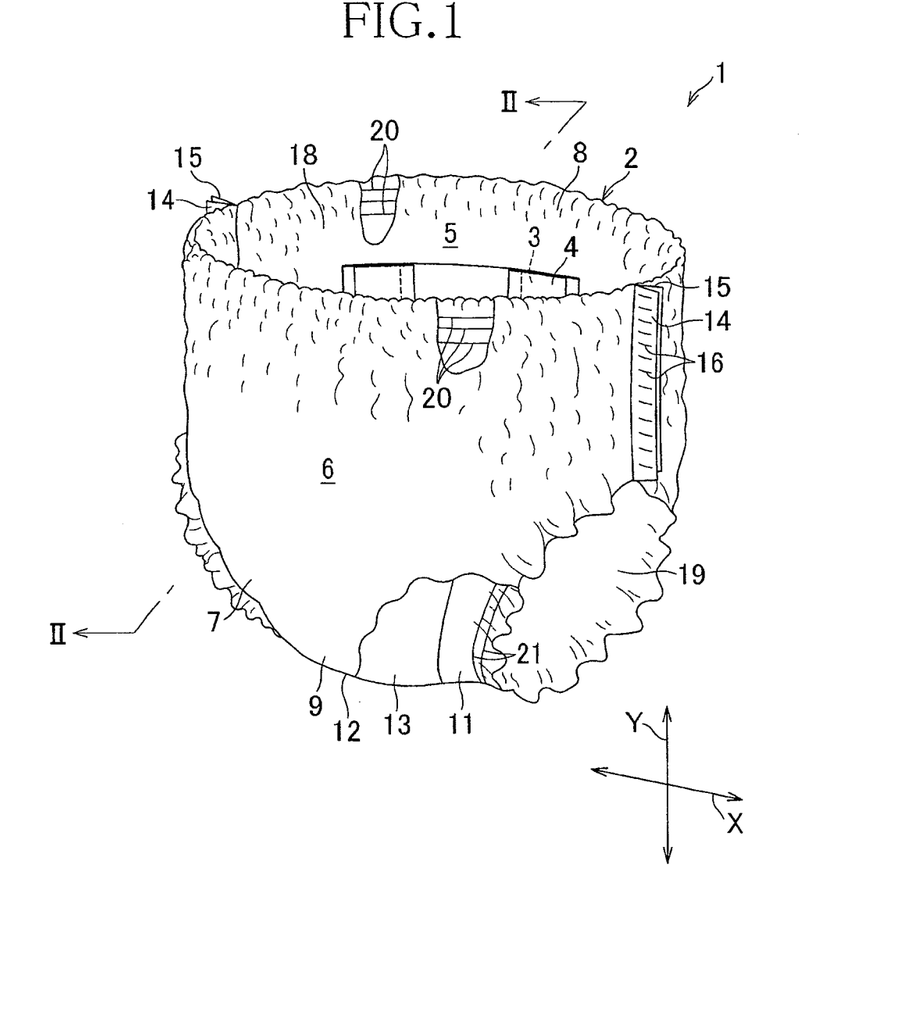
FIG. 1 is a perspective view of a diaper as a first embodiment according to the invention.

FIGS. 1 through 7 illustrate a first embodiment according to the invention. FIG. 1 shows a diaper 1 as put on a wearer's body wherein the diaper 1 is partially cut off for convenience of illustration. As shown, the diaper 1 comprises a liquid-absorbent chassis 2, a barrier sheet 3 and leak-barrier cuffs 4. The chassis 2 is pants-shaped and defined by a transverse direction X, a vertical direction Y, a longitudinal direction Y, an inner side 5 facing a wearer's skin, an outer side 6 facing wearer's clothes, a front waist region 7, a rear waist region 8 and a crotch region 9 extending between said front and rear waist regions 7, 8. The chassis 2 comprises a topsheet 11, a backsheet 12 and a liquid-impervious leak-barrier sheet 13 sandwiched between these top- and backsheets 11, 12.

The front and rear waist regions 7, 8 respectively have pairs of side edges 14, 15 put flat and joined together at a plurality of joints 16 arranged intermittently along the respective side edges 14, 15 to form seams. In this way, the front and rear waist regions 7, 8 are joined together along the respective side edges 14, 15 so as to form a waist-opening 18 surrounded by the front and rear waist regions 7, 8 and a pair of leg-openings 19 surrounded by the respective rows of joints 16 and the crotch region 9. A plurality of waist elastic members 20 circumferentially extend along a peripheral edge of the waist-opening 18 and a plurality of leg elastic members 21 circumferentially extend along respective peripheral edges of the leg-openings 19. These elastic members 20, 21 are sandwiched between the topsheet 11 and the backsheet 12 and bonded under tension to at least one of these sheets 11, 12 by means of adhesive (not shown).

Figure 2:
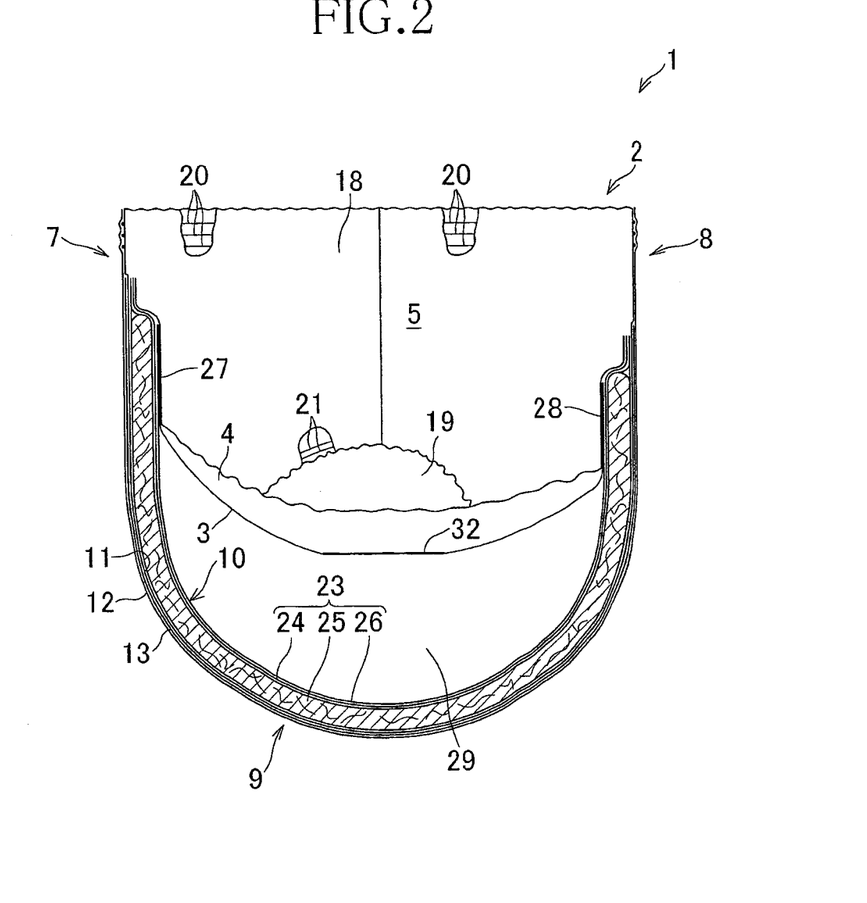
FIG. 2 is a sectional view taken along a line II-II in FIG. 1.

FIG. 2 is a sectional view taken along a line II-II in FIG. 1 and partially cut away for convenience of illustration. As will be seen in FIG. 2, the liquid-absorbent structure 10 is disposed on the inner side 5 of the chassis 2 facing a wearer's skin, the barrier sheet 3 is disposed on the side of the liquid-absorbent structure 10 facing the wearer's skin, and the leak-barrier cuffs 4 is disposed on the side of the barrier sheet 3 facing the wearer's skin. While the liquid-absorbent structure 10 extends across the crotch region 9 and further into the front and rear waist regions 7, 8 in the longitudinal direction Y in this embodiment, the liquid-absorbent structure 10 will effectively function so far as it extends at least across the crotch region 9. The liquid-absorbent structure 10 includes a liquid-absorbent panel 23 disposed on the inner surface of the topsheet 11.

The liquid-absorbent panel 23 comprises a liquid-absorbent core 25 wrapped with a liquid-absorbent and spreadable sheet 24 such as tissue paper and an inner sheet 26 covering the liquid-absorbent and -spreadable sheet 24. The side of the liquid-absorbent panel 23 facing wearer's clothes is covered with the leak-barrier sheet 13 which is disposed on the inner surface of the backsheet 12 to prevent bodily fluids once absorbed by the core 25 from leaking out from the diaper 1. The leak-barrier sheet 13 may be bonded directly to the bottom surface of the liquid-absorbent panel 23.

The barrier sheet 3 is bonded in the vicinity of its front and rear ends 27, 28 to the inner sheet 26 by means of adhesion or sealing. The front end 27 and the rear end 28 are located in the front waist region 7 and the rear waist region 8, respectively. In a pants-shaped state as illustrated, the crotch region 9 is bowed and the barrier sheet 3 is spaced upward from the inner sheet 26 in the longitudinal direction Y under contraction of barrier sheet's elastic members which will be described later. The front and rear ends 27, 28 of the barrier sheet 3 are bonded to the inner sheet 26 so that the barrier sheet 3 as a whole takes a posture like a hammock being slung. As a result, a pocket 29 is defined between the barrier sheet 3 and the liquid-absorbent panel 23. The leak-barrier cuffs 4 are spaced upward from the barrier sheet 3 under contraction of cuffs' elastic members which will be described later and form a wall extending in the longitudinal direction Y.

Figure 3:
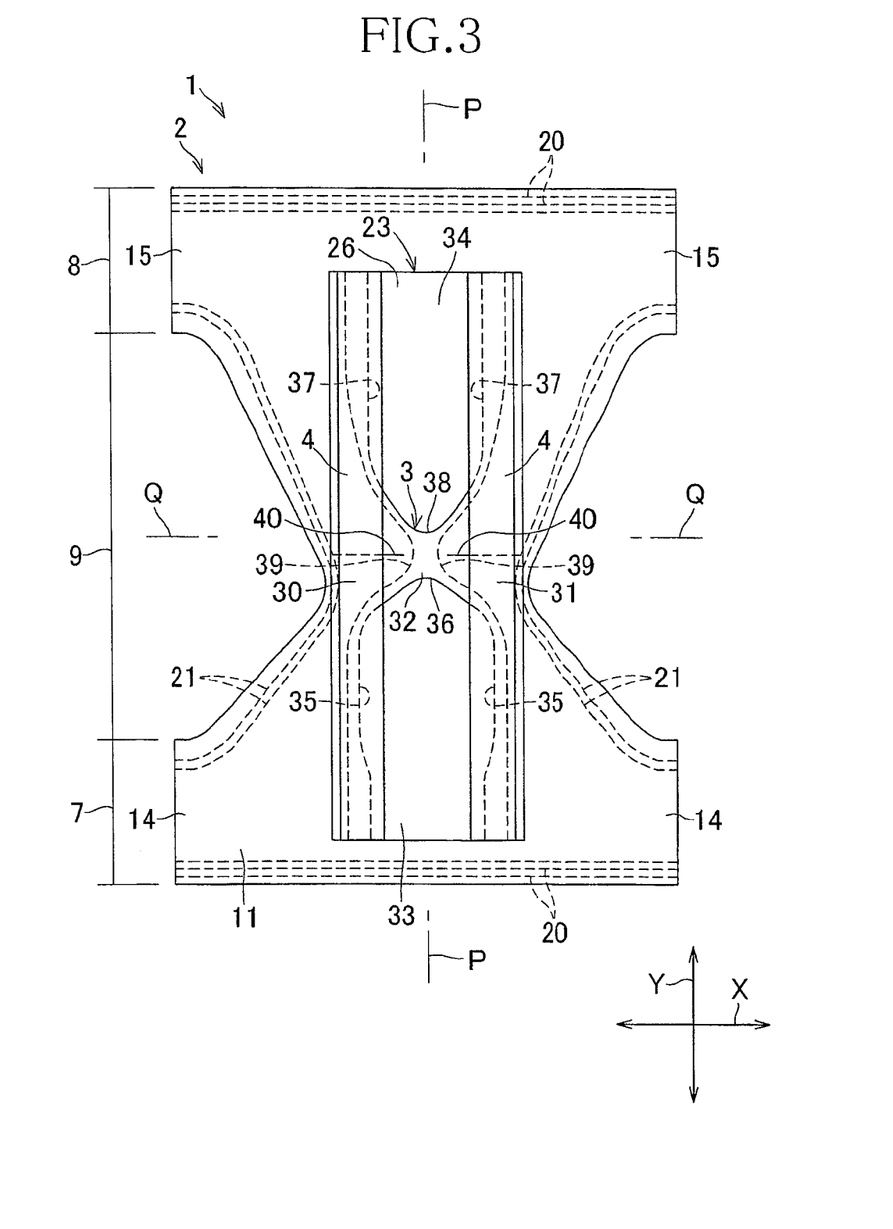
FIG. 3 is a plan view showing the diaper of FIG. 1 as has been flatly developed.

FIG. 3 is a plan view of the diaper 1 as flatly developed in the longitudinal direction Y as well as in the transverse direction X after the front and rear waist regions 7, 8 have been separated from each other along the respective rows of the joints 16 as seen in FIG. 1. In the state of the diaper 1 shown herein, the respective elastic members are under tension so as to keep the diaper 1 in the flattened state. The diaper 1 has a longitudinal center line P-P bisecting a dimension of the diaper 1 in the transverse direction X and a transverse center line Q-Q bisecting a dimension of the diaper 1 in the longitudinal direction Y and is bilaterally-symmetric about the longitudinal center line P-P.

The chassis 2 has a concave shape curved inwardly and the liquid-absorbent panel 223 is rectangular and laminated on the topsheet 11 of the chassis 2. The barrier sheet 3 comprises a pair of lateral zones 30, 31 opposed to and spaced from each other in the transverse direction X and a middle zone 32 extending between these lateral zones 30, 31 wherein the middle zone 32 is located in the crotch region 9. The lateral zones 30, 31 cooperate with the middle zone 32 to form front and rear through-holes 33, 34. The front through-hole 33 has a substantially U-shape extending from the middle zone 32 into the front waist region 7 and the rear through-hole 34 has a substantially U-shape extending from the middle zone 32 into the rear waist region 8. The front through-hole 33 is defined by a pair of inner side edges 35 of the respective lateral zones 30, 31 and a curved margin of closure 36 connecting these inner side edges 35 to each other. The rear through-hole 34 is defined by a pair of inner side edges 37 of the respective lateral zones 30, 31 and a curved margin of closure 38 connecting these inner side edges 37 to each other.

These curved margins of closure 36, 38 of the front and rear through-holes 33, 34 are defined by the middle zone 32 of the barrier sheet 3.

The leak-barrier cuffs 4 comprise a pair of sheets extending in the longitudinal direction Y in symmetric relationship about the longitudinal center line P-P and formed, for example, by nonwoven fabric or plastic film which is preferably liquid-impervious. The leak-barrier cuffs 4 are formed so as to overlap respective skin-contacting surfaces of the lateral zones 30, 31 of the barrier sheet 3. Each of the leak-barrier cuffs 4 has a dimension in the transverse direction X substantially same as or slightly larger than a dimension of the individual lateral zone 30, 31 of the barrier sheet 3 in the transverse direction X.

This diaper 1 may be put on a wearer's body with the wearer's external genital opposed to the front through-hole 33, the wearer's anus opposed to the rear trough-hole 34 and a zone of the wearer's skin defined between the external genital and the anus opposed to the middle zone 32. With the diaper 1 put on a wearer's body in this manner, the margin of closure 36 of the front through-hole 33 is preferably positioned aside forward from the transverse center Q-Q and the margin of closure 38 of the rear through-hole 34 is preferably positioned just on or in the vicinity of the transverse center line Q-Q. Thereupon, the liquid-absorbent panel 23 is bowed in the longitudinal direction Y and the barrier sheet 3 lifted up into contact with a wearer's skin under contraction of the barrier sheet's elastic members 39 so that the pocket 29 (See FIG. 2) may be formed between the barrier sheet 3 and the liquid-absorbent panel 23. In this way, body waste may be reliably received by the pocket 229 through the front and rear through-holes 33, 34 and thus prevented from coming in direct contact with the wearer's skin.

Figure 4:
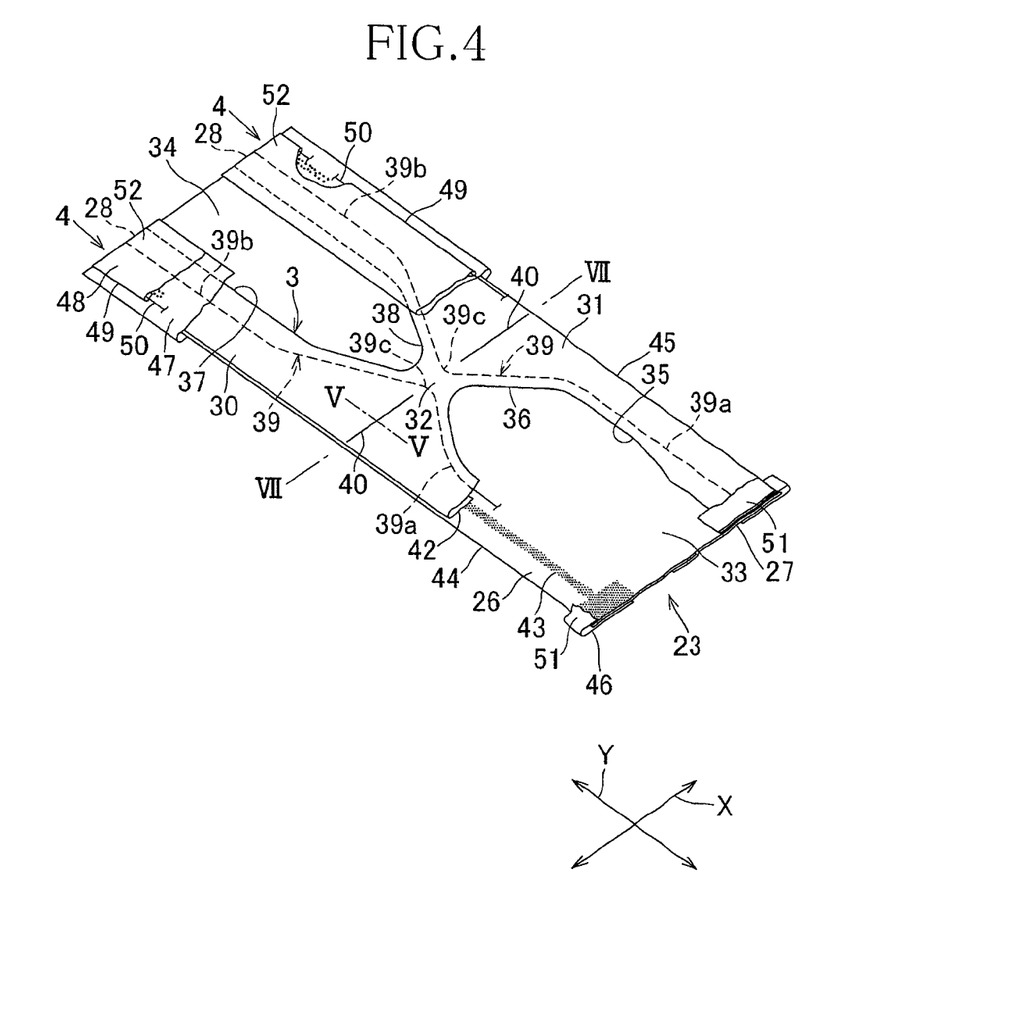
FIG. 4 is a schematic diagram illustrating an important part as seen in FIG. 3.
Figure 5:
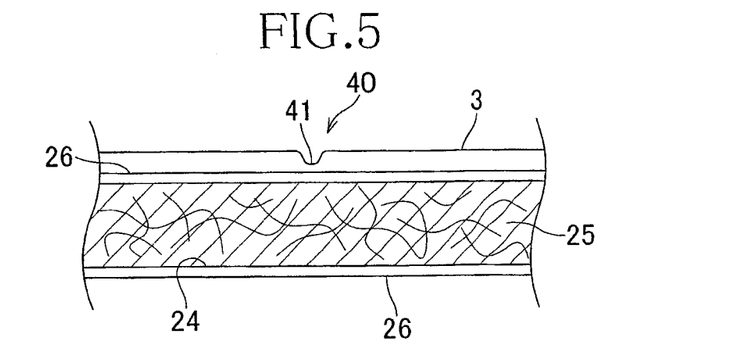
FIG. 5 is a sectional view taken along a line V-V in FIG. 4.

FIG. 4 is a diagram illustrating details of the liquid-absorbent panel 23, the barrier sheet 3 and the leak-barrier cuffs 4 but partially cutaway for convenience of illustration. The lateral zones 30, 31 of the barrier sheet 3 are folded back toward the liquid-absorbent panel 23 and form folded zones 42, so as to define two-ply structures. The folded zones 42 are bonded to inner sheet 26 of liquid-absorbent panel 23 via joint zones 43. Each of these two-ply lateral zones 30, 31 contains therein the barrier sheet's elastic member 39 bonded thereto by means of adhesive (not shown). Specifically these barrier sheet's elastic members 39 are attached to the respective lateral zones 30, 31 under tension in the longitudinal direction Y.

The front and rear through-holes 33, 34 have substantially U-shapes extending from the middle zone 32 toward the front and rear waist regions 7, 8 and defined by substantially rectilinear inner side edges 35, 37 and the curved margins of closure 36, 38. The barrier sheet's elastic members 39 are provided along the front and rear through-holes 33, 34. Specifically, each of the barrier sheet's elastic members 39 comprises a substantially rectilinear front segment 39a extending in the vicinity of the inner side edge 35 of the front through-hole 33 and a substantially rectilinear rear segment 39b in the vicinity of the inner side edge 37 of the rear through-hole 34. In the middle zone 32 connecting the front and rear through-holes 33, 234 with each other, the elastic member 39 has a convex segment 239c extending toward the longitudinal center line P-P.

The barrier sheet 3 is provided outside the convex segments 39c as viewed in the transverse direction X with folds 40 extending in the transverse direction X. These folds 40 are formed by thermal processing including fusion and application of pressure. These folds 40 are formed outside the middle zone 32 so as to extend in the transverse direction X. Each of the folds 40 is dimensioned in the transverse direction X so as to be substantially the same as the dimension of the barrier sheet's elastic member 39 as measured from the convex segment 39c to the side edge of the barrier sheet 3. As will be seen in FIG. 5 which is a sectional view taken along a line taken along a line V-V in FIG. 4, said fold 40 is provided in the form of a groove 41 formed by thermal processing under a pressure so as to guide operation of folding the barrier sheet 3.

As will be seen in FIG. 4, the joint zones 43 extend from the front end 27 to the rear end 28 in the longitudinal direction Y inside the side edges 44, 45 of the liquid-absorbent panel 23 as viewed in the transverse direction X. Specifically, the joint zones 43 are spaced from the side edges 44, 45, respectively. These joint zones 43 are typically formed by conventional type of rubber-based hot melt adhesive but it is also possible to form these joint zones 243 by means of commonly used means such as sonic sealing or heat-sealing technique.

Each of the leak-barrier cuffs 4 comprises a three-ply sheet having a Z-shaped cross section. More specifically, the leak-barrier cuff 4 comprises a first layer 46, a second layer 47 and a third layer 48 laminated one upon another. The first layer 46 is sandwiched between the liquid-absorbent panel 23 and the chassis 2. The second layer 47 is folded back from the first layer 46 onto the side of the barrier sheet 3 facing a wearer's skin so as to be placed upon the lateral zone 30 or 31. The third layer 48 is folded back from the second layer 47 onto the side of the second layer 47 facing the wearer's skin. In this manner, the leak-barrier cuff 4 is folded back toward the wearer's skin in the order of the first, second and third layers 46, 47, 48 wherein the first layer 46 and the second layer 47 are placed upon each other via the liquid-absorbent panel 23 and the second layer 47 is placed directly upon the third layer 48. The third layer 48 is folded back onto itself along a side edge 49 thereof so that a cuff's elastic member 50 may be attached thereto. The cuff's elastic member 50 is bonded to this two-ply side edge 49 under tension in the longitudinal direction Y.

At front and rear ends 51, 52 of the leak-barrier cuff 4, the first layer 46 is bonded to the liquid-absorbent panel 23, the second layer 47 is bonded to the barrier sheet 3 and the third layer 48 is bonded to the second layer 47. The first layer 46 is bonded to the topsheet 11 of the chassis 2 so as to extend in the longitudinal direction Y between the front and rear ends 51, 52 and thereby to form a fixed edge. Under contractile force of the cuff's elastic member 50 exerted on the leak-barrier cuff 4, the second layer 47 and the third layer 48 are unfolded and thereby spaced upward from the barrier sheet 3 so as to form a wall as seen in FIG. 2. Portions of the second layer 47 and the third layer 48 adapted to be spaced from the barrier sheet 3, i.e., not bonded to the barrier sheet 3 is referred to herein as a free edge.

Figure 6:
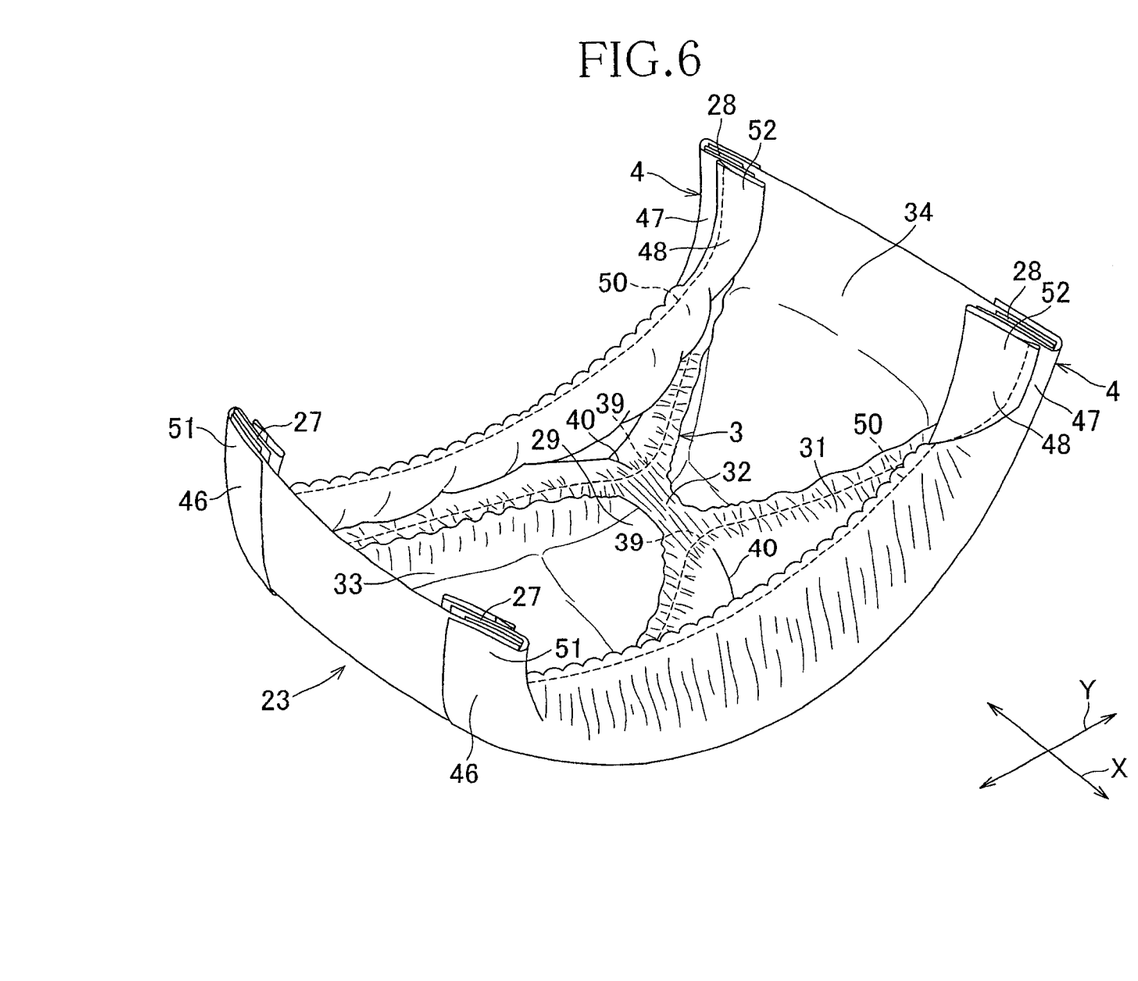
FIG. 6 is a schematic diagram illustrating the important part in FIG. 4 as put on a wearer's body.

FIG. 6 illustrates the barrier sheet 3, the leak-barrier cuffs 4 and the liquid-absorbent panel 23 when such diaper is put on a wearer's body. With the diaper put on a wearer's body, as illustrated, the barrier sheet's elastic members 39 as well as the cuffs' elastic members 50 contract. Contraction of the barrier sheet's elastic members 39 causes the liquid-absorbent panel 23 to be bowed and simultaneously causes barrier sheet 3 to be spaced upward from the liquid-absorbent panel 23. Contraction of the cuffs' elastic members 50 causes the free edges of the second layer 47 as well as the third layer 48 of the leak-barrier cuffs 4 to be unfolded in the direction in which these layers are spaced from the liquid-absorbent panel 23 and to be raised from their collapsed states.

When the liquid-absorbent panel 23 is bowed as has been described above, the barrier sheet 3 bonded thereto is also subjected to a force tending to bow this barrier sheet 3 in the longitudinal direction Y. The barrier sheet 3 are formed with the folds 40 which are, in turn, formed with grooves 41 facilitating the barrier sheet 3 to be folded along the folds 40 as the liquid-absorbent panel 23 is bowed. Thus the barrier sheet 3 is folded so as to be convex toward the liquid-absorbent panel 23. The folds 40 are formed outside the convex segments 39c of the barrier sheet's elastic members 39 as viewed in the transverse direction X. Consequentially, contractile force of the barrier sheet's elastic members 39 directed from the lateral zones 30, 31 toward the longitudinal center line P-P is exerted on the middle zone 32 of the barrier sheet 3, further facilitating the lateral zones 30, 31 along the folds 40.

Figure 7:
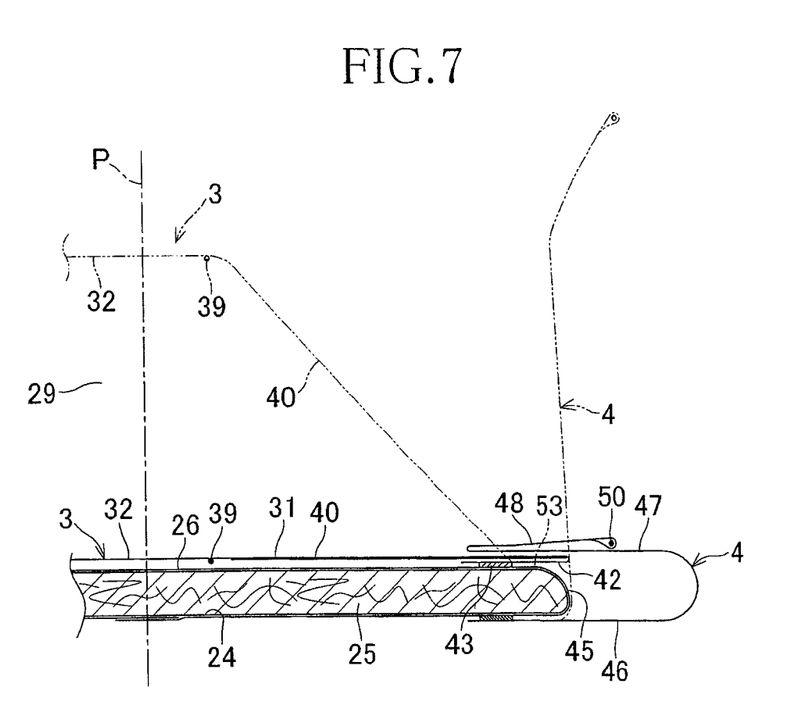
FIG. 7 is a sectional view taken along a line VII-VII in FIG. 4.

FIG. 7 is a sectional view taken along a line VII-VII in FIG. 4 wherein chain double-dashed lines indicate the diaper put on a wearer's body as shown in FIG. 6. While FIG. 7 illustrates the lateral zone 31 of the barrier sheet 3, it will be appreciated that the lateral zone 230 is similar to the lateral zone 31. Contraction of the barrier sheet's elastic members 39 causes the middle zone 32 of the barrier sheet 3 is spaced upward from the liquid-absorbent panel 23 into contact with a wearer's skin. Outside the middle zone 32 formed with the folds 40 as viewed in the transverse direction X, the barrier sheet 3 is folded along these folds 40 so as to slope from the middle zone 32 toward the liquid-absorbent panel 23.

The barrier sheet 3 is bonded to the liquid-absorbent panel 23 via the joint zones 43. The joint zones 43 lie inside the side edges 44, 45 of the liquid-absorbent panel 23 as viewed in the transverse direction X and therefore, when the barrier sheet 3 is spaced upward from the liquid-absorbent panel 23, a portion of the liquid-absorbent panel 23 not covered with both the barrier sheet 3 and the leak-barrier cuffs 4, i.e., an exposed portion 53 is defined between the side edges 44, 45 and the joint zones 43. Urine otherwise staying on the barrier sheet 3 can be guided along the folds 40 to the liquid-absorbent panel 23 and absorbed therein. In this way, even if urination occurs onto the barrier sheet 3, such urine can be quickly guided from the barrier sheet 3 to the liquid-absorbent panel 23, the wearer can be protected from any skin trouble due to urine staying on the barrier sheet 3.

The joint zones 43 are formed so as to overlap the respective free edges of the leak-barrier cuffs 4 in collapsed states thereof. Specifically, the joint zones 43 are located so as to overlap the second layer 47 and the third layer 48, respectively. If the joint zones 43 are located so as to overlap the fixed edges, the zones defined between the joint zones 43 and the side edges 44, 45 will be covered with the leak-barrier cuffs 4 when the leak-barrier cuffs 4 rise and the exposed zone 53 of the liquid-absorbent panel 23 will not be formed. In view of this, the joint zones 43 should be located so as to overlap the free edges.

Outside the exposed zone 53 of the liquid-absorbent panel 23 as viewed in the transverse direction X, the leak-barrier cuffs 4 raise themselves from the side edges 44, 45 of the liquid-absorbent panel 23. In this way, urine guided to said exposed zone 53 can be prevent from leaking out from the diaper. In the region of the barrier sheet's elastic members 39 overlapping the leak-barrier cuffs 4, the barrier sheet' elastic members 39 would not come in direct contact with a wearer's skin and skin irritation can be correspondingly alleviated.

According to this embodiment, the folds 40 are formed by thermal processing. The lateral zones 30, 31 are folded back and opposed surfaces of the respective lateral zones 30, 31 folded back in this manner are joined together, for example, by heat sealing to form folds extending in the transverse direction X. With applying an adhesive on the side of barrier sheet 3 facing a wearer's skin, the lateral zones 30, 31 can be folded and fixed to form folds. There may be provided between the barrier sheet 3 and the inner sheet 26 the partition sheet adapted to partition the pocket into the front pocket defined in the front waist region 7 and the rear pocket defined in the rear waist region 8 to form the folds. In this case, one end of the partition sheet is bonded to the barrier sheet 3 and the other end is bonded to the inner sheet 26 so that the barrier sheet 3 spaced from the chassis is pulled toward the chassis in the joint zone of the partition sheet and the folds are formed in the zone pulled in this manner. Specifically, in the zone of the barrier sheet 3 pulled in this manner, the barrier sheet 3 is spaced from the chassis by a distance less than the remaining zone of the barrier sheet 3. In consequence, the barrier sheet 3 is formed on its zone pulled toward the chassis with the fold which is convex toward the chassis. The barrier sheet 3 having differential fiber fineness also can be used and therefore differential stiffness to form the fold.

While the single fold 40 is provided in the lateral zones 30, 31, respectively, according to this embodiment, in the respective lateral zones 30, 31 a plurality of folds extending in parallel one to another can be provided or the single folds on each of the lateral zones 30, 31 can be connected to each other to form a single fold 40 continuously extending over the two lateral zones 30, 31.

While the barrier sheet's elastic members 39 including the convex segments 39c are used according to this embodiment, the barrier sheet's elastic members 239 comprising two elastic members 39 intersecting with each other in the middle zone 32 or the barrier sheet' elastic members 39 divided in the longitudinal direction Y in the middle zone 32 also can be used.

While there are provided the front and rear through-holes 33, 34 according to this embodiment, one of these front and rear through-holes 33, 34 may be eliminated or these through-holes may be circumferentially closed in the front and rear waist regions 7, 8, respectively. In other words, these through-holes are not limited U-shaped through-holes but, for example, may be O-shaped, respectively.

While the barrier sheet 3 and the leak-barrier cuff 4 respectively comprise single sheets according to this embodiment, it is possible to form them by adhesively joining a pair of sheets, respectively. In this case, the barrier sheet's elastic member 39 as well as the cuff's elastic member 50 may be sandwiched between a pair of sheets, respectively. The folds 40 may be formed on one of these two sheets or on both sheets after they have been laminated together.

Second Embodiment According to the Invention

Figure 8:
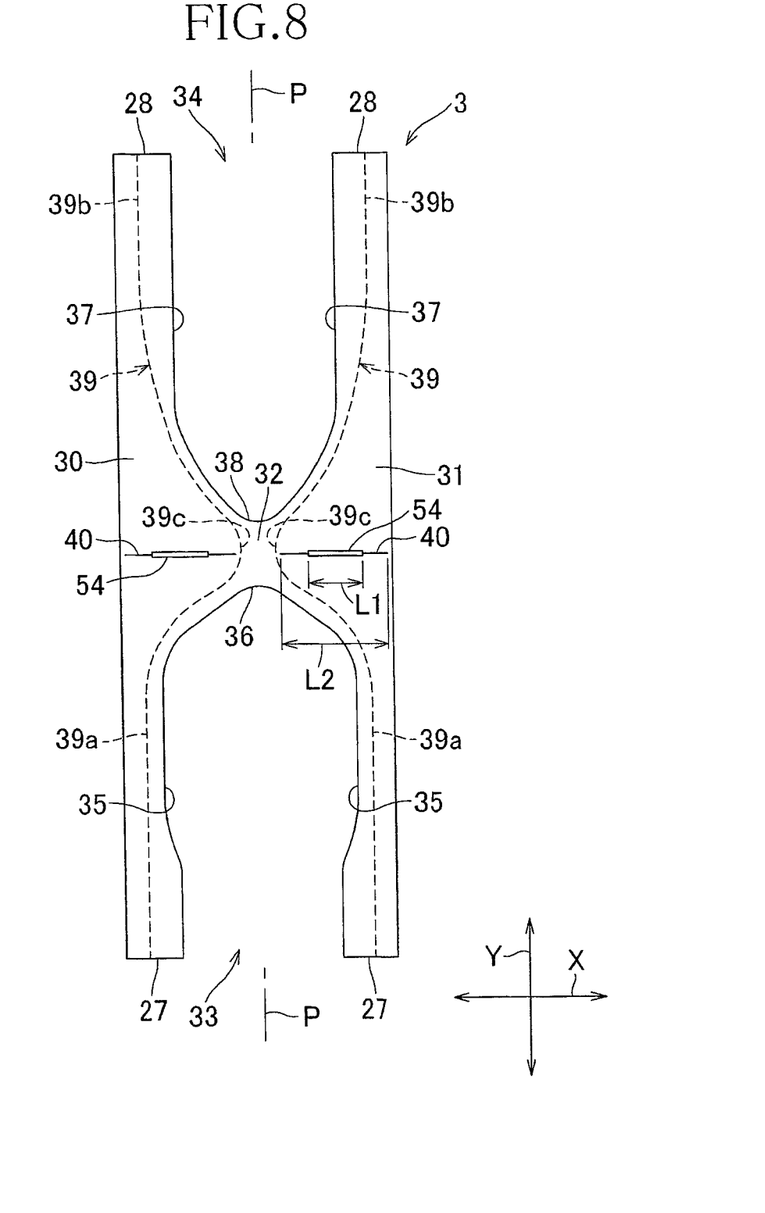
FIG. 8 is a schematic diagram illustrating an important part in the second embodiment according to the third aspect of the invention.

FIG. 8 illustrates a second embodiment according to the invention. This embodiment is similar to the first embodiment except that the barrier sheet is provided with slits 54. The other features are similar to those in the first embodiment and will not be described in details.

According to this second embodiment, the barrier sheet 3 is formed with slits 54. These slits 54 extend through the barrier sheet 3 in its thickness direction. The slits 54 are formed by partially cutting out the respective folds 40 so as to extend on the respective folds 40 in the transverse direction X. Each of the slits 54 has a length dimension L1 in the transverse direction X substantially corresponding to ½ of a length dimension L2 from the convex segment 39c of barrier sheet's elastic member 39 to the side edge of the barrier sheet 3. If the length dimension L1 of the slit 54 exceeds this, s strength of the barrier sheet 3 will be deteriorated. The fold 40 has a length dimension substantially same as the length dimension L2.

According to this second embodiment, the zones in which the slits 254 are formed have a sufficiently low rigidity to facilitate the barrier sheet 3 to be folded. On both sides of the slit 54 in the transverse direction X, the fold 40 is contiguous to this slit 54. The fold 40 cooperates with the slit 54 to facilitate the barrier sheet 3 to be folded.

The slit 54 extends through the barrier sheet 3 in the thickness direction, allowing urine staying on the barrier sheet 3 to be guided through the slit 54 to the liquid-absorbent panel 23. Urine staying on the barrier sheet 3 can be more quickly guided to the liquid-absorbent panel 23 than in the case of the barrier sheet 3 provided with only the folds 40.

While the slit 54 is rectangular according to this embodiment, the shape of the slit 54 is not limited to this but may have other various shapes such as an elliptical shape extending in the transverse direction X. Even when the folds 40 have been formed by thermal processing, the slits 54 may be formed so as to overlap the folds 40 to alleviate any skin irritation due to the presence of the folds 40.

According to the invention, the barrier sheet 3 as well as the leak-barrier cuffs 4 may be formed, for example, by liquid-impervious and air-permeable nonwoven fabric, the topsheet 11 as well as the backsheet 12 may be formed, for example, by air-permeable nonwoven fabric, the leak-barrier sheet 13 may be formed, for example, by plastic film and the liquid-absorbent core 25 constituting the liquid-absorbent panel 23 may be formed, for example, by a mixture of fluff pulp and super-absorbent polymer particles. All of these materials have conventionally been used in the related field of technique.

The invention claimed is:

1. An absorbent article comprising:
    a chassis having a front-to-rear direction and a transverse direction, a longitudinal center line bisecting a dimension of said chassis in the transverse direction, a wearer's skin facing side and a wearer's skin non-facing side,
    a front waist region,
    a rear waist region,
    a crotch region extending between said front and rear waist regions,
    a liquid-absorbent structure disposed on said crotch region, and
    a barrier sheet provided in said crotch region on the wearer's skin facing side and being able to be spaced from said chassis;
    wherein said barrier sheet has
        a pair of lateral zones extending in said front-to-rear direction and opposed to each other in said transverse direction,
        a middle zone connecting said lateral zones to each other,
        front and rear ends extending in said transverse direction and opposed to each other in said front-to-rear direction, and
        elastic members extending in said front-to-rear direction and having a convex segment extending toward said longitudinal center line in said middle zone and attached under tension to said barrier sheet and opposed to each other in said transverse direction, wherein
    said front and rear ends are permanently bonded to the wearer's skin facing side of said chassis and said liquid-absorbent structure is adapted to be bowed in a direction from said crotch region toward said front and rear waist regions and thereby to form a pocket between said barrier sheet and said liquid-absorbent structure,
    said pair of lateral zones and said middle zone define through-holes so that body waste can pass said through-holes into said pocket, said pair of lateral zones lying outside said middle zones as viewed in said transverse direction includes portions being thermally processed under pressure to form folds along which said barrier sheet is convex toward said chassis, and said folds have a pair of slits in the barrier sheet extending in the transverse direction and each of said slits has a length dimension in the transverse direction substantially corresponding to ½ of a length dimension from said convex segment of said elastic member to a side edge of said barrier sheet.

2. The article according to claim 1, wherein said liquid-absorbent structure includes side edges extending in the front-to-rear direction and opposed to each other in the transverse direction, said liquid-absorbent structure is bonded to said lateral zones of said barrier sheet at joint zones and said joint zones lie inside the side edges as viewed in said transverse direction, the liquid-absorbent structure further includes exposed portions between the side edges and the joint zones and configured not to be covered with said barrier sheet when said barrier sheet is spaced upward from said chassis.

3. The article according to claim 1, wherein said through-hole comprises a front through-hole in a front of said middle zone as viewed in said front-to-rear direction and a rear through-hole in a rear of said middle zone as viewed in said front-to-rear direction, said elastic members are attached to said barrier sheet along said front and rear through-holes, and said folds lie outside said elastic members as viewed in said transverse direction.

4. The article according to claim 1, wherein the length dimension of said each slit is less than that of each of the folds.

5. The article according to claim 1, wherein said pair of slits extends through the barrier sheet in a thickness direction.

* * * * *